US00PP09827P

United States Patent [19]

Spira et al.

[11] Patent Number: Plant 9,827

[45] Date of Patent: Mar. 18, 1997

[54] ASIAN PEAR TREE NAMED 'ASIO 2'

[75] Inventors: Joel S. Spira; Ruth R. Spira, both of Coopersburg; Eugene S. Konno, Germansville; Neil J. Vincent, Quakertown, all of Pa.

[73] Assignee: Subarashii Kudamono Co., Inc., Coopersburg, Pa.

[21] Appl. No.: 531,183

[22] Filed: Sep. 19, 1995

[51] Int. Cl.[6] ..... A01H 5/00

[52] U.S. Cl. ..... Plt./36

[58] Field of Search ..... Plt./36

*Primary Examiner*—James R. Feyrer

*Attorney, Agent, or Firm*—Burns, Doane, Swecker & Mathis

[57] ABSTRACT

A new and distinct variety of Asian Pear, botanically known as *Pyrus pyrifolia* is provided. The new cultivar forms attractive large to extra large substantially round fruit having a golden brown russet surface with prominent lenticels and a distinctive rich sweet flavor. The tree is large and exhibits a vigorous well-branched and spreading growth habit. The leaves are dark green in coloration with pinnate moderately-branched venation. Picking of the fruit commonly can begin during mid-September at Coopersburg, Pa., U.S.A. Substantial and consistent fruit crops are formed.

3 Drawing Sheets

SUMMARY OF THE INVENTION

The present invention comprises a new and distinct cultivar of Asian Pear, botanically known as *Pyrus pyrifolia*, and hereinafter is referred to by the cultivar name 'Asio 2'.

The new cultivar germinated from a seed as a distinctive seedling during the summer of 1983 while growing in a test orchard at 1506 Pleasant View Road, Coopersburg, Pa., U.S.A. The new cultivar was discovered among many open-pollinated seedlings of the 'Chojuro' cultivar (non-patented in the United States) that were growing for test purposes. The seed that produced the new cultivar of the present invention was formed at Coopersburg, Pa., U.S.A. The male parent of the new cultivar is unknown. A large number of Asian Pear varieties were growing in the area as well as a few varieties of European Pear. It is impossible to identify the parent plants of the new cultivar. A single tree of the new cultivar was discovered in the test orchard following selective study and initially was designated No. 223.

Since 1987 the original tree of the new cultivar has annually produced a crop of high quality Asian Pears.

It was found that the new 'Asio 2' cultivar of the present invention:

(a) forms attractive early mid-season large to extra large substantially round fruit having a golden brown russet surface with prominent lenticels and a rich sweet flavor,
(b) forms a large tree having a vigorous well-branched and spreading growth habit, and
(c) forms generally elliptical dark green leaves with moderate venation.

Asexual reproduction of the new cultivar by budding on 'Bartlett' rootstock carried out at Aspers, Pa., U.S.A. beginning during 1987, has demonstrated that the characteristics of the new cultivar as herein disclosed are firmly fixed and are retained through successive generations of such asexual propagation.

It was found that the 'Asio 2' cultivar flowers substantially concurrently with the 'Chojuro' cultivar (non-patented in the United States), but matures approximately one week later than the 'Chojuro' cultivar. The roundish shape of the fruit is similar to that of 'Chojuro' cultivar; however, the fruit of the new cultivar is of a lighter golden brown coloration with prominent lenticels while the fruit of the 'Chojuro' cultivar is darker with more red and possesses inconspicuous lenticels. Also, the fruit of the 'Chojuro' cultivar exhibits a different more winey flavor.

'Asio 2 ' has not been observed under all possible environmental conditions to date. Accordingly, it is possible that the phenotype may vary somewhat with variations in the environment, such as temperature, light, day length, contact with pesticides, etc.

The new variety of the present invention will be marketed under the JunoSan trademark.

BRIEF DESCRIPTION OF THE PHOTOGRAPHS

The accompanying photographs show in color as nearly true as it is reasonably possible to make the same in color illustrations of this character the original tree of the new variety as well as plant parts thereof. The spreading tree was approximately 11 years of age and was growing on its own roots at 1506 Pleasant View Road, Coopersburg, Pa., U.S.A. All photographs with the exception of FIG. 6 were taken on Sep. 14, 1994.

Figure 6:
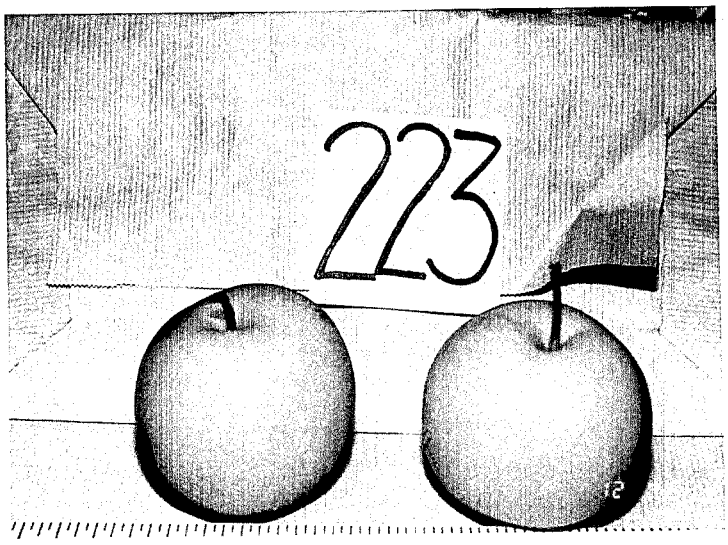

FIG. 6 illustrates additional specimens of the fruit of the new variety that were harvested during September, 1994, placed in refrigerated storage at approximately 32° F., and removed from such storage and photographed on Dec. 4, 1994. During such storage the fruit surface assumed a darker coloration (as illustrated). A measuring stick in inches is provided at the extreme lower portion of the photograph for comparative purposes.

DETAILED DESCRIPTION

The chart used in the identification of the colors described hereafter is The R.H.S. Colour Chart of The Royal Horticultural Society, London, England. In some instances common color terms are used which are to be accorded their ordinary dictionary significance. The trees described were being grown under standard orchard conditions at Coopersburg, Pa., U.S.A.

Classification:

*Botanical.*—*Pyrus pyrifolia* (*P. serotina*), cv. 'Asio 2'.

*Commercial.*—Asian Pear.

Tree:

*Size.*—Large. The original tree at the age of 12 years is approximately 15 feet tall. Three years following the field planting of a tree that was budded 1½ years earlier on 'Bartlett' rootstock, a tree height of approximately 6 feet commonly will be observed. Five years following field planting of a tree that was budded 1½ years earlier on 'Bartlett' rootstock, a tree height of approximately 9 feet commonly will be observed, and predominantly upright. However, unspread branches commonly will naturally settle to angles of approximately 70 degrees under the weight of a heavy fruit load.

*Growth habit.*—Vigorous.

*Configuration.*—Spreading.

*Density.*—Dense and well-branched.

*Hardiness.*—Hardy in wood and bud.

*Fruit bearing.*—Very productive.

*Bearing habit.*—Annually on second-year and older wood with the fruit being borne laterally and terminally on second year and older shoots, as well as laterally on spurs.

*Trunk.*—Medium diameter and medium texture.

*Branches.*—Thickness: medium. Frequency: commonly with a moderate branching density with approximately 4 to 6 branches typically originating per every two feet of trunk. Branch angles: the angles of the main scaffold branches commonly are approximately 45 to 60 degrees under natural growing conditions. When limb spreaders are employed, branch angles of approximately 90 degrees can be achieved thereby resulting in earlier fruit bearing. Bark texture: smooth (as illustrated). Bark color: greenish brown on younger wood and dark olive on older wood. Internodal length: tends to be short (e.g., approximately 2.2 cm). Lenticels: prominent and a lighter tan in coloration.

Figure 1:
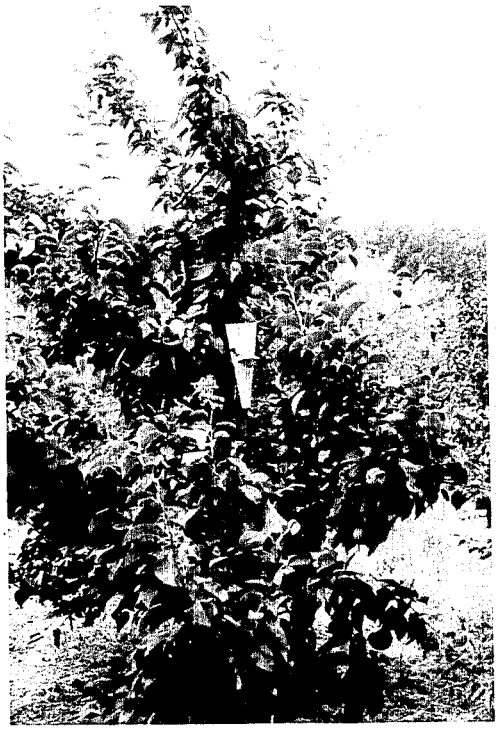
FIG. 1 illustrates the entire tree of the new variety wherein the large tree size and vigorous growth habit are apparent.
Figure 2:
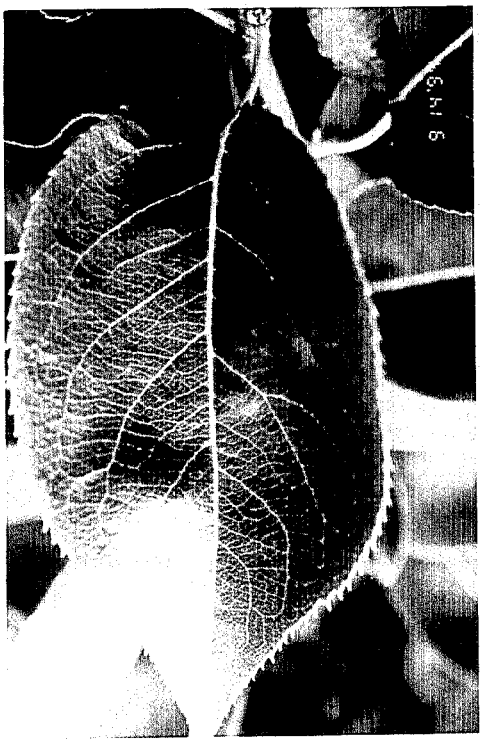
FIG. 2 illustrates a typical generally elliptical leaflet of the new variety wherein the serration pattern and moderate venation are more readily apparent. The illustrated leaf is believed to lack the maturity of the leaves illustrated in FIGS. 3, 4, and 5, and accordingly is of a lighter green coloration.
Figure 3:
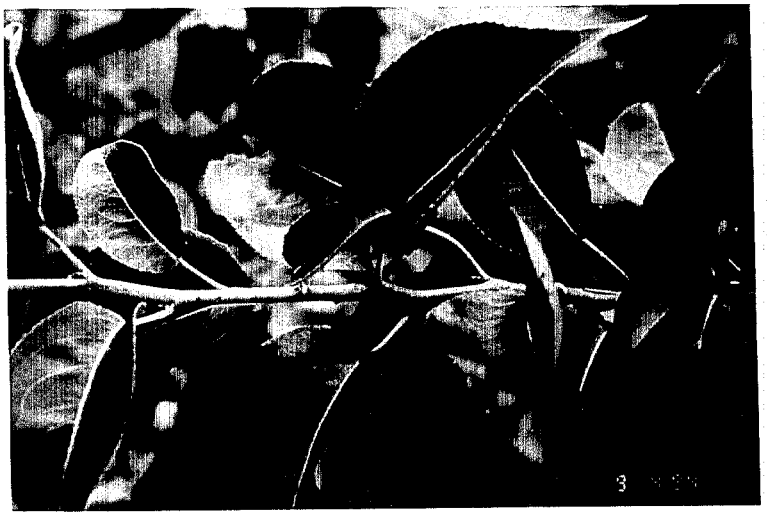
FIG. 3 illustrates a typical limb of the new variety wherein the generally elliptical ovate leaves with serrated edges are apparent.
Figure 4:
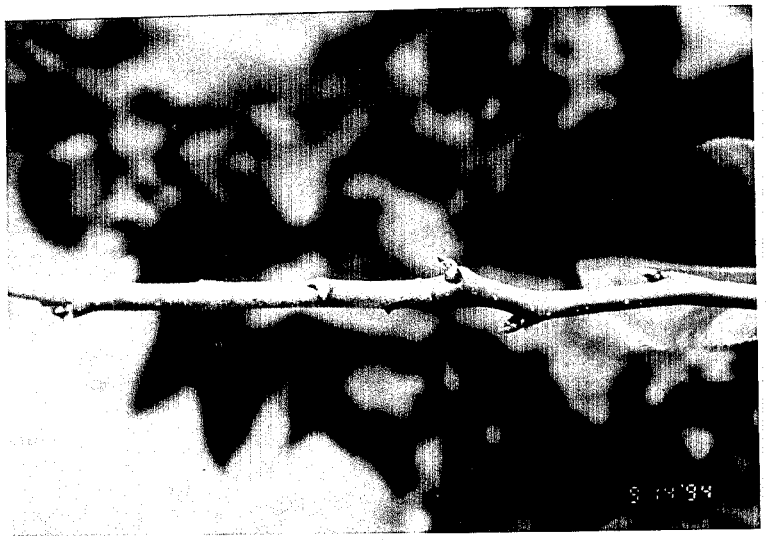
FIG. 4 illustrates a typical limb of the new variety wherein the leaves have been removed so that the smooth appearance of the limb is unobstructed.
Figure 5:
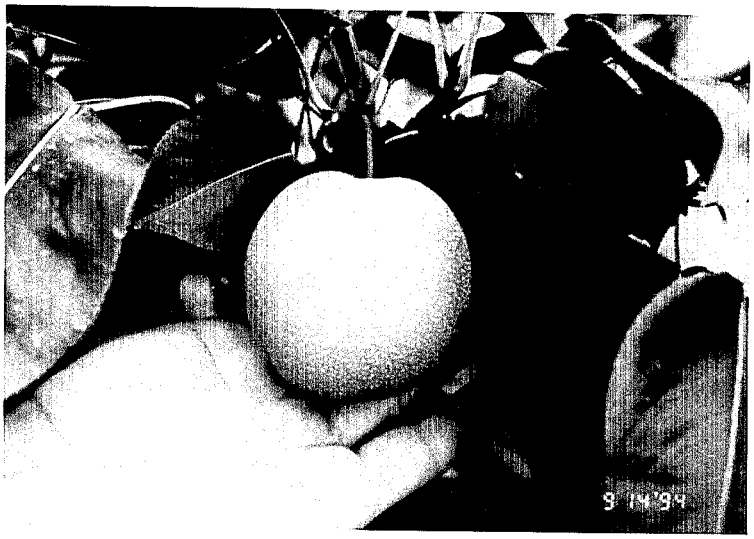
FIG. 5 illustrates a typical specimen of fruit of the new variety prior to full maturity together with typical foliage while present on the tree.

*Leaves.*—Size: medium, commonly approximately 8.2 cm. in length on average. Configuration: generally elliptical. Base: rounded. Apex: acute. Margin: serrulate (as illustrated in FIG. 2). When the leaves are subjected to close inspection and compared to those of the 'Chojuro' cultivar, it is found that the 'Asio 2' cultivar displays more serrations that are closer together and are less deeply cut. Venation: pinnate, and moderately branched. Thickness: medium. Color upper surface: during a typical growing season is dark green, Green Group 136B, and during the fall Yellow-Orange Group 21B. Color under surface: during a typical growing season is silvery green, Green Group 137D, and during the fall Yellow-Orange Group 22B. Petiole: short, and commonly approximately 2.4 cm. in length.

*Flowers.*—Season: mid-season, and generally concurrent with the 'Chojuro' cultivar. During 1993, the first bud break occurred on April 16th, and full bloom occurred on April 30th. During 1994, the first bud break occurred on April 15th, and full bloom occurred on April 25th. Size: medium, and commonly approximately 3.2 cm. in diameter on average. Color: white, White Group 155A. Pollen: viable pollen is produced which has enabled 'Asio 2' to be utilized as a pollen parent in interspecific crosses that have been carried out annually since 1988. When attempts have been made to self-pollinate 'Asio 2', no resulting fruit has set to date. Accordingly, the preliminary indications are that 'Asio 2' may be self-infertile. bearing: commonly in a corymb of 6 to 8 flowers. Configuration: the reproductive organs are similar to those of the 'Chojuro' cultivar. The flowers generally possess five pistils and bear fruit having five sets of carpels. However, some flowers have been observed having six pistils. When six pistils are present, one pistil commonly is substantially shorter than the others, but is viable as evidenced by the recovery of fruit specimens bearing approximately 11 to 12 seeds.

*Fruit.*—Season of maturity: early mid-season maturing approximately one week later than the 'Chojuro' cultivar. During 1993, the first picking was on September 15th and the last picking was on September 30th. During 1994, the first picking was on September 18th and the last picking was on September 27th. Bearing: most of the fruit is borne laterally on spurs; however, some fruit also can be produced terminally on shoots. Size: large to extra large, and commonly approximately 8 to 10 cm. in diameter. The fruit weight commonly ranges from approximately 275 to 375 grams. It is recommended that the fruit be thinned in order to encourage the formation of the larger-sized fruit. Configuration: substantially round. Neck: absent. Stem: medium in length (e.g., approximately 2.5 cm. on average), and substantially uniform in thickness and thinning slightly towards the point of abscission. Cavity: shallow, acute, and approximately 1.2 cm. in width. Basin: moderately wide (e.g., approximately 2.5 cm.). Calyx: open, and deciduous. Skin: light green ground cover with golden brown russet surface and numerous prominent lighter tan lenticels (as illustrated). The fruit additionally is completely russeted. At maturity an overall fruit coloration approaching Greyed-Orange Group 165B commonly is displayed. The tan lenticels commonly range in coloration between Greyed-Orange Group 164B and 165D. Flesh: very juicy, white, and crisp. Flavor: sweet (TSS 11 to 13 Brix), and rich. The distinctive fruit flavor of the new cultivar is unlike the more winey flavor of the 'Chojuro' cultivar. Such fruit flavor is believed to be substantially uniform throughout the fruit. Core: distant. Carpels: elliptical, with axial symmetry. Seeds: commonly 6 to 10 per fruit, commonly 1 or 2 per carpel, medium-sized, commonly flattened on one side, and dark brown in coloration. Quality: very good to excellent. Keeping quality: excellent, can be stored at least 3 months in good condition at 32° F. Fire blight resistance: no inoculations for fire blight screening have been carried out; however, it is believed that at least some resistance to fire blight is being exhibited. For instance, when fire blight strikes have occurred in the orchard where 'Asio 2' was being grown, no fire blight has been observed in 'Asio 2'.

We claim:

1. A new and distinct cultivar of Asian Pear, substantially as illustrated and described, which:

(a) forms attractive early mid-season large to extra large substantially round fruit having a golden brown russet surface with prominent lenticels and a rich sweet flavor, (b) forms a large tree having a vigorous well-branched and spreading growth habit, and (c) forms generally elliptical dark green leaves with moderate venation.

* * * * *